(12) United States Patent
Amemiya

(10) Patent No.: US 6,933,934 B2
(45) Date of Patent: Aug. 23, 2005

(54) TIME-GAIN CONTROLLING METHOD AND APPARATUS, RECORDING MEDIUM AND ULTRASONIC IMAGING APPARATUS

(75) Inventor: Shinichi Amemiya, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 548 days.

(21) Appl. No.: 10/000,687

(22) Filed: Oct. 31, 2001

(65) Prior Publication Data

US 2002/0087218 A1 Jul. 4, 2002

(30) Foreign Application Priority Data

Dec. 28, 2000 (JP) ........................................ 2000-400840

(51) Int. Cl.[7] ................................................ G09G 5/00
(52) U.S. Cl. ........................ 345/179; 367/87; 600/437
(58) Field of Search .................... 345/179; 367/87–116; 600/437, 443, 447, 459; 382/128; 700/85

(56) References Cited

U.S. PATENT DOCUMENTS

| | | | | |
|---|---|---|---|---|
| 5,315,999 A | * | 5/1994 | Kinicki et al. .............. | 600/443 |
| 5,841,889 A | * | 11/1998 | Seyed-Bolorforosh ...... | 382/128 |
| 5,862,049 A | * | 1/1999 | Sato et al. .................... | 700/85 |
| 5,891,038 A | * | 4/1999 | Seyed-Bolorforosh et al. .. | 600/447 |
| 6,468,212 B1 | * | 10/2002 | Scott et al. ................. | 600/437 |
| 6,645,148 B2 | * | 11/2003 | Nguyen-Dinh et al. ..... | 600/459 |

* cited by examiner

Primary Examiner—Sumati Lefkowitz
Assistant Examiner—Srilakshmi K Kumar
(74) Attorney, Agent, or Firm—Moonray Kojima

(57) ABSTRACT

In order to perform precise time-gain control using a small manual setting device, one of two-dimensional coordinates of a position on a surface of a tablet pointer 215 which an external object touches is defined as a coordinate on a time axis, and the other as a coordinate on a gain axis; and the time gain is controlled based on the two-dimensional coordinates. In order to provide an ultrasonic imaging apparatus that responds to the requirement for both portability and versatility, the ultrasonic imaging apparatus comprises a portable imaging apparatus 100 comprising ultrasonic imaging means, and a support apparatus 500 which comprises supporting means for supporting extension of functions of the imaging apparatus, and which is electrically connected to and mechanically joined to the imaging apparatus so that it can be removably combined with the imaging apparatus.

20 Claims, 19 Drawing Sheets

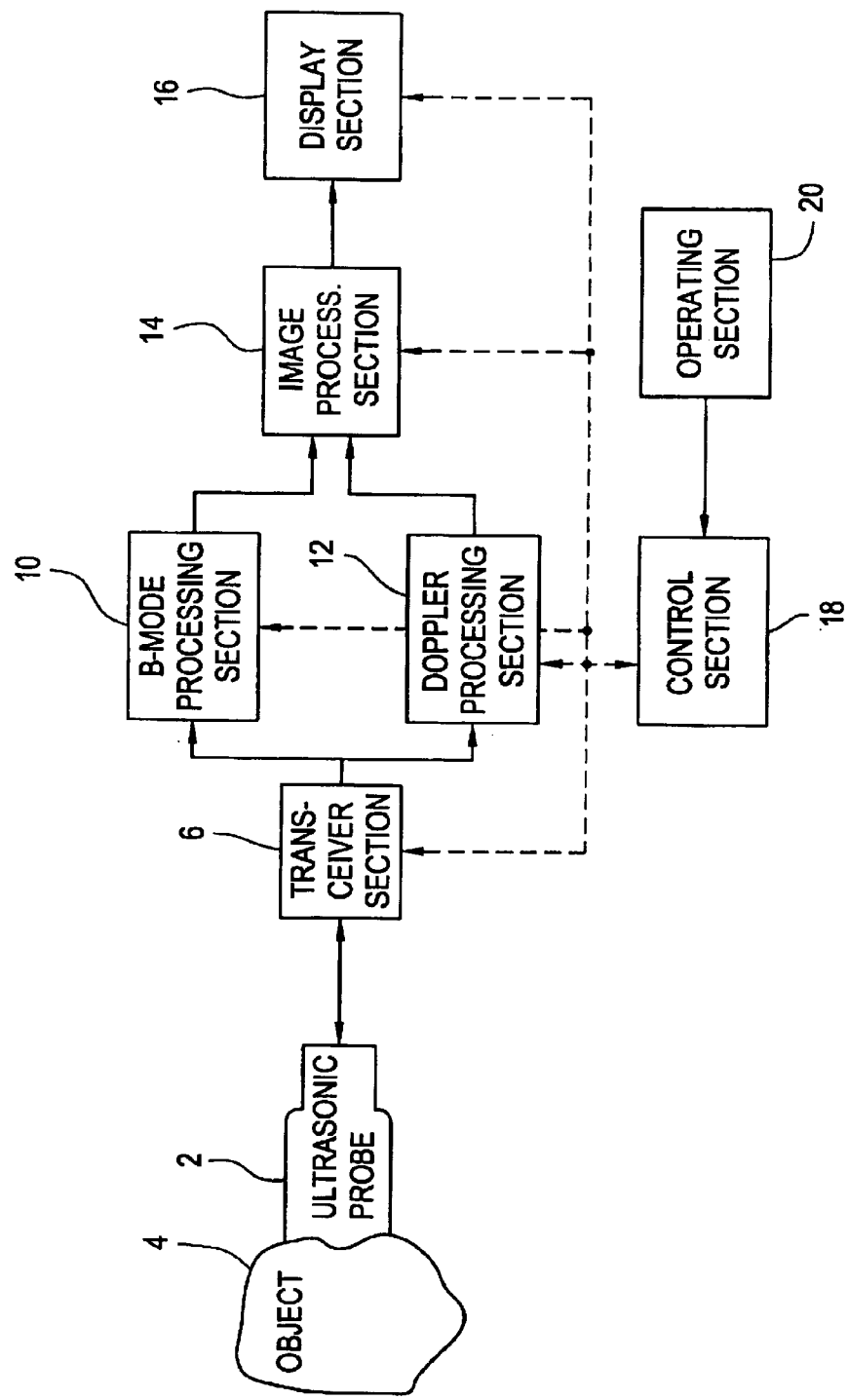

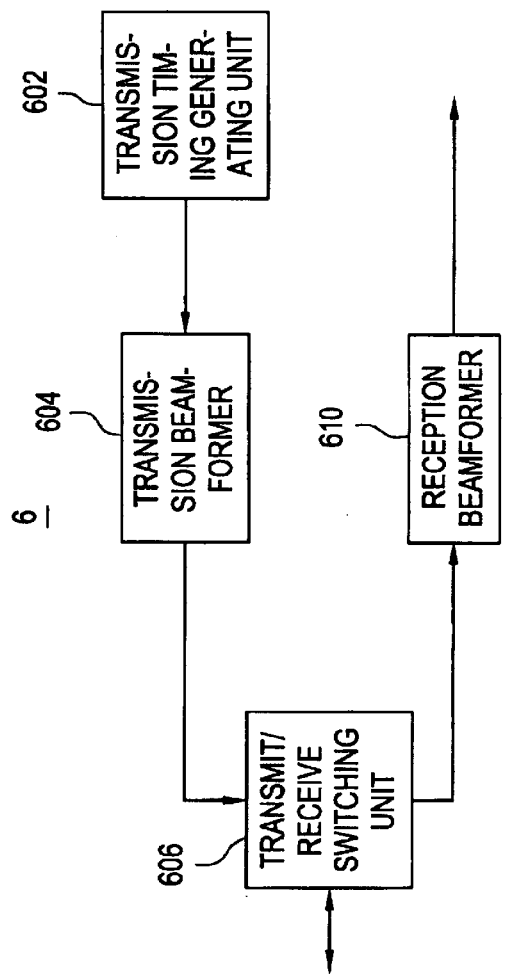
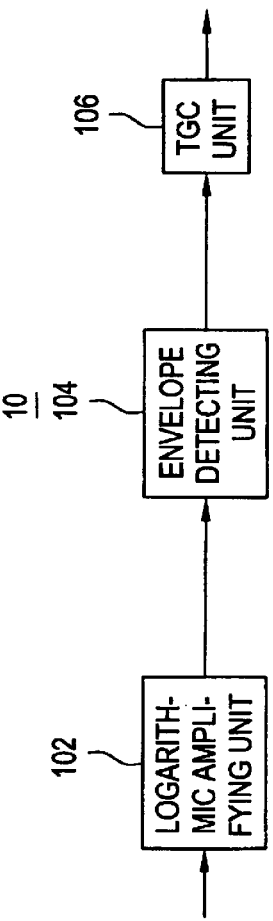

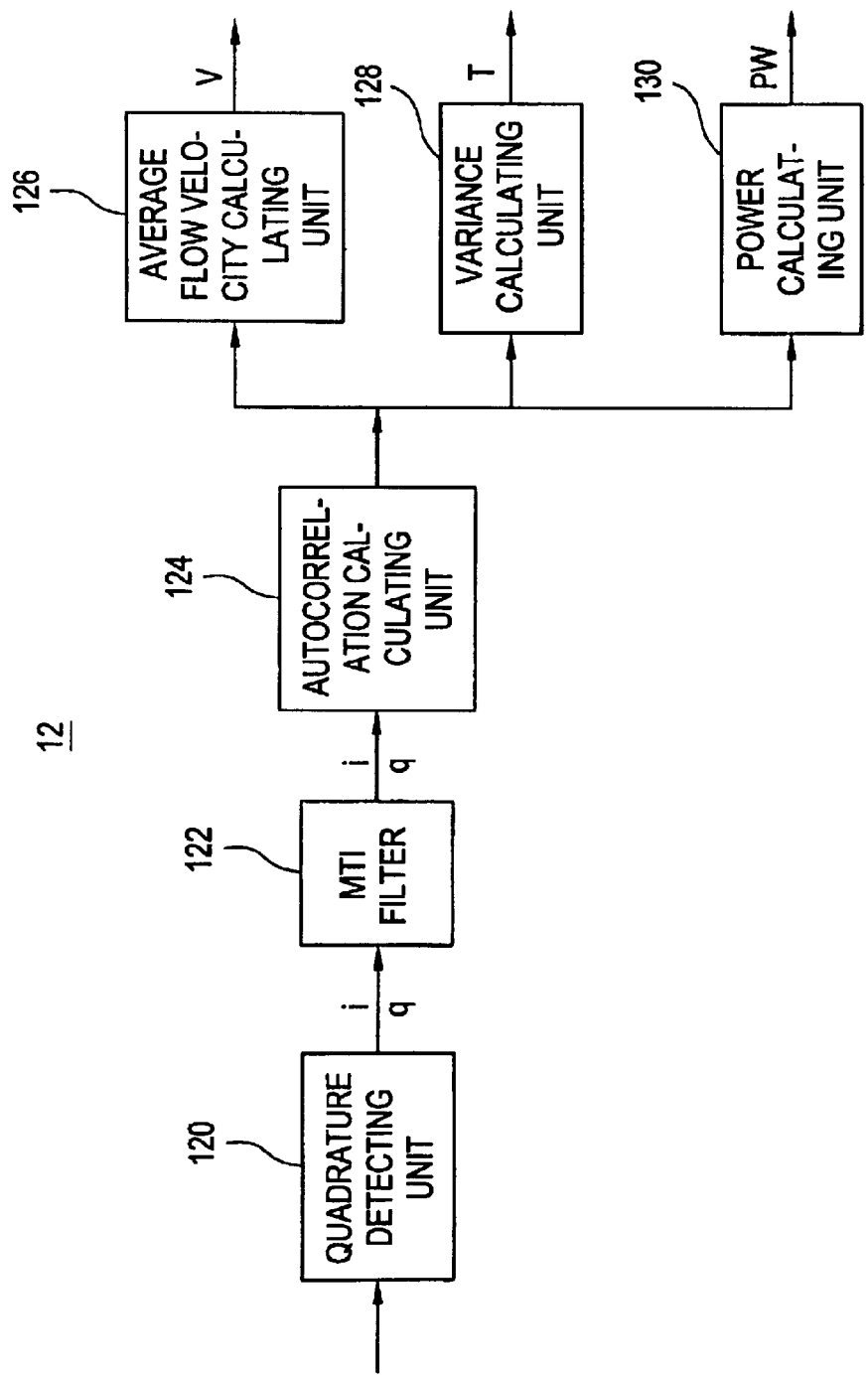

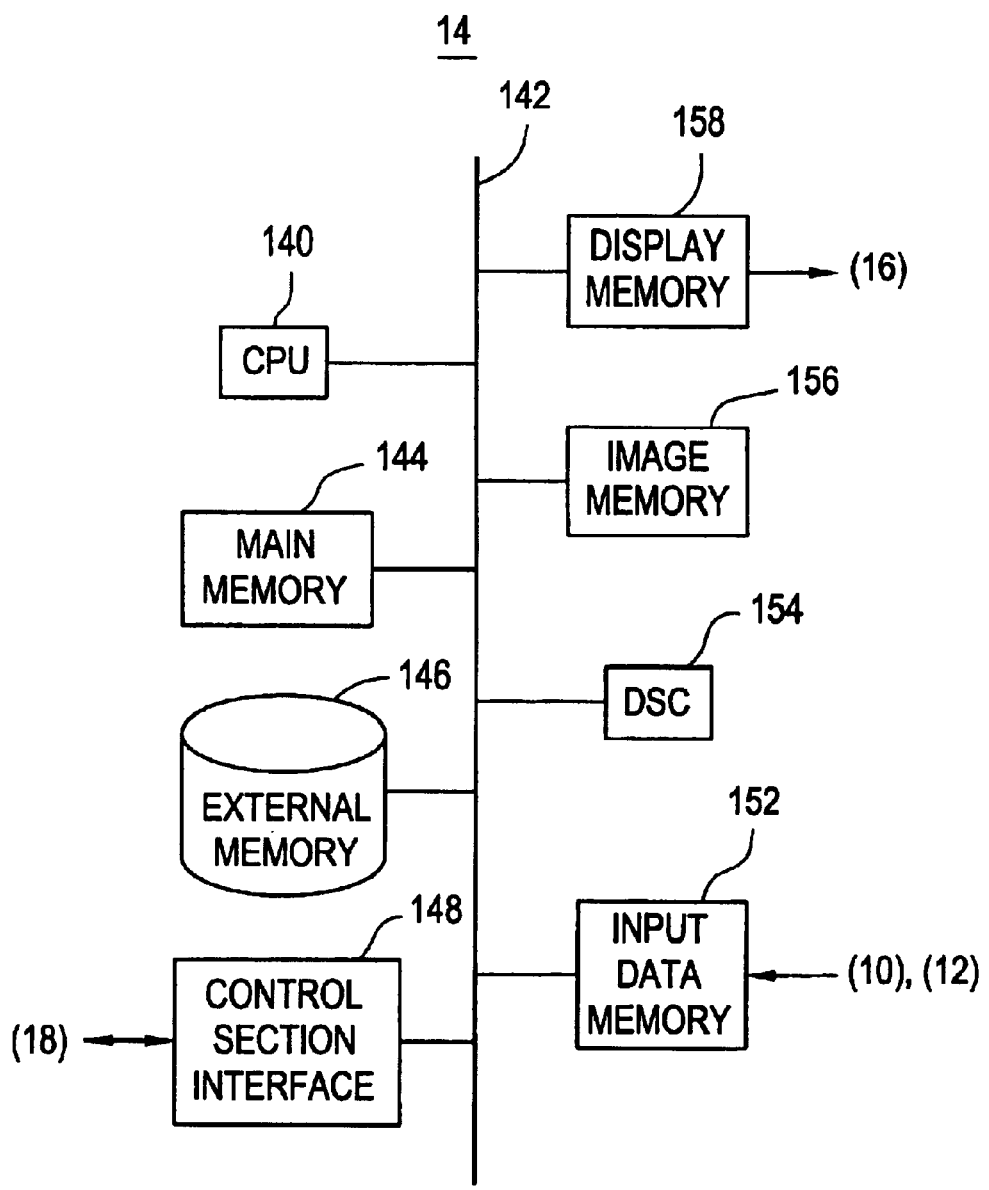

POSITION TYPE

RATE TYPE

COMBINATION TYPE

Setting by Manual Drawing

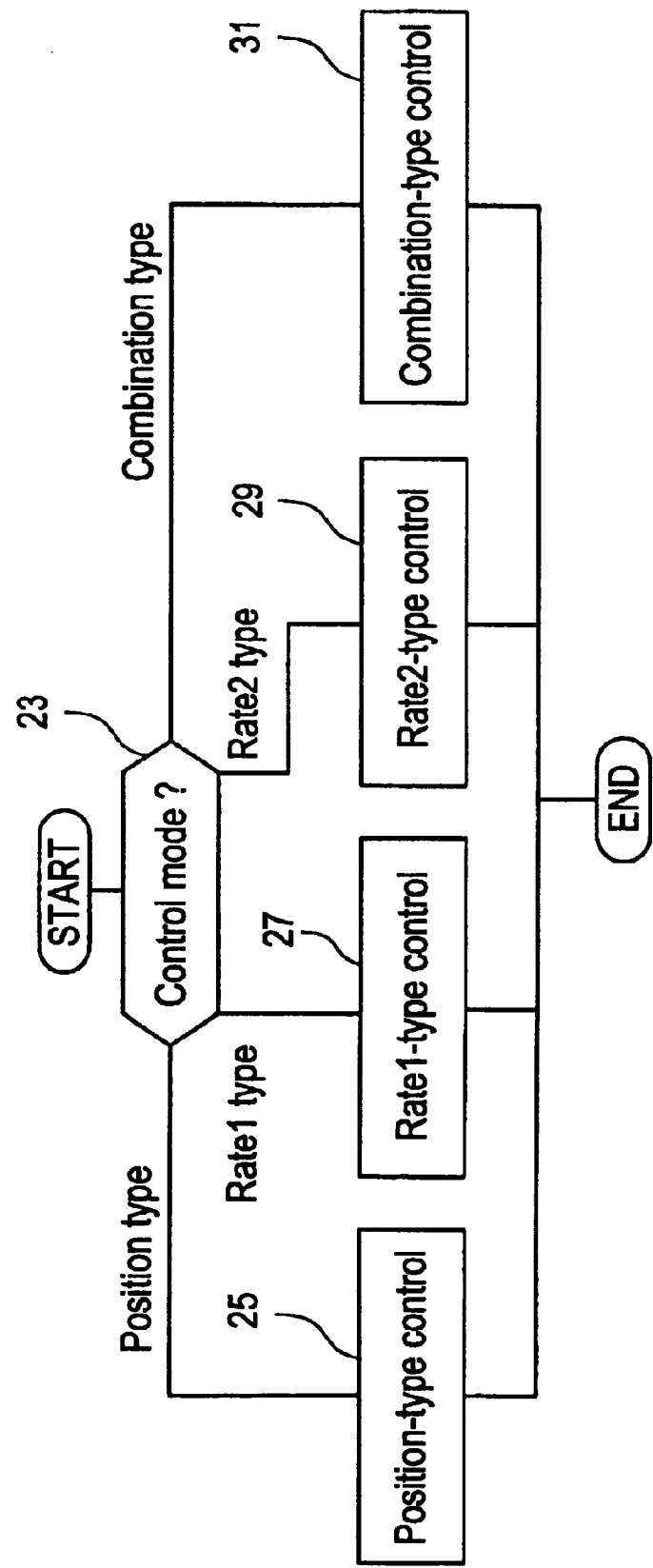

TIME-GAIN CONTROLLING METHOD AND APPARATUS, RECORDING MEDIUM AND ULTRASONIC IMAGING APPARATUS

BACKGROUND OF THE INVENTION

The present invention relates to a time-gain controlling method and apparatus, recording medium and ultrasonic imaging apparatus, and particularly to a method and apparatus for controlling the time gain for echo reception, a medium recorded with a program for causing a computer to implement such a time-gain controlling function, and an ultrasonic imaging apparatus comprising such a time-gain controlling apparatus.

RELATED ART

An ultrasonic imaging apparatus scans the interior of an object to be imaged; receives echoes; and produces a B-mode image corresponding to the intensity of the echoes for display.

In receiving the echoes, time-gain control (TGC) is performed. The TGC controls the gain for the echo reception depending upon the echo return time, i.e., the depth of the reflection point of an echo, to correct the brightness of the B-mode image so that the brightness is prevented from decreasing as the depth increases.

A time-gain curve of the TGC, i.e., a curved line representing the relation ship between the depth of an echo reflection point and the gain, can be manually set by the user.

The manual setting device is configured with a slide volume for gain setting. A plurality of the slide volumes are provided in combination and each slide volume is assigned a gain setting function for a different depth.

Such a manual setting device, however, requires a large space for the plurality of slide volumes in an operating section of the ultrasonic imaging apparatus. If the number of slide volumes is decreased to save space, the precision of the TGC is reduced due to a decrease in the number of points for controlling the time gain curve.

SUMMARY OF THE INVENTION

It is therefore an object of the present invention to provide a method and apparatus for performing precise time-gain control using a small manual setting device, a medium recorded with a program for causing a computer to implement such a time-gain controlling function, and an ultrasonic imaging apparatus comprising such a time-gain controlling apparatus.

(1) The present invention, in one aspect thereof for solving the aforementioned problem, is a time-gain controlling method for controlling a time gain for echo reception, comprising the steps of: defining one of two-dimensional coordinates of a position on a surface of a tablet pointer which an external object touches as a coordinate on a time axis, and defining the other as a coordinate on a gain axis; and controlling the time gain based on the two-dimensional coordinates.

(2) The present invention, in another aspect thereof for solving the aforementioned problem, is a time-gain controlling apparatus for controlling a time gain for echo reception, comprising: a tablet pointer; coordinate translating means for defining one of two-dimensional coordinates of a position on a surface of the tablet pointer which an external object touches as a coordinate on a time axis, and defining the other as a coordinate on a gain axis; and controlling means for controlling the time gain based on the two-dimensional coordinates.

(3) The present invention, in still another aspect thereof for solving the aforementioned problem, is a recording medium recorded in a computer-readable manner with a program for causing a computer to implement the functions of: in controlling a time gain for echo reception, defining one of two-dimensional coordinates of a position on a surface of a tablet pointer which an external object touches as a coordinate on a time axis, and defining the other as a coordinate on a gain axis; and controlling the time gain based on the two-dimensional coordinates.

(4) The present invention, in still another aspect thereof for solving the aforementioned problem, is an ultrasonic imaging apparatus comprising ultrasound transmitting means for transmitting ultrasound, echo receiving means for receiving echoes of the transmitted ultrasound, time-gain controlling means for controlling a time gain for the reception, image producing means for producing an image based on echo signals subjected to the time-gain control, and display means for displaying the produced image, wherein the time-gain controlling means comprises: a tablet pointer; coordinate translating means for defining one of two-dimensional coordinates of a position on a surface of the tablet pointer which an external object touches as a coordinate on a time axis, and defining the other as a coordinate on a gain axis; and controlling means for controlling the time gain based on the two-dimensional coordinates.

According to the invention in the aforementioned aspects, one of two-dimensional coordinates of a position on a surface of a tablet pointer which an external object touches is defined as a coordinate on a time axis and the other as a coordinate on a gain axis, and the time-gain is controlled based on the two-dimensional coordinates; and therefore precise time-gain control can be achieved using a small manual setting device.

In the invention in the aforementioned aspects, it is preferred to perform the control by determining the gain depending upon the value of the coordinate on the gain axis, in that a time-gain curve can be set as drawn by a user on the surface of the tablet pointer.

Moreover, in the invention in the aforementioned aspects, it is preferred to perform the control by increasing the gain corresponding to a coordinate on one side with respect to a reference coordinate on the gain axis, and decreasing the gain corresponding to a coordinate on the other side, in that manual adjustment of a gain curve by a user is made easy.

In this case, it is preferred that the change rate of the gain be constant, in that the manual adjustment is made easier.

On the other hand, it is alternatively preferred that the change rate of the gain correspond to a difference between the aforementioned coordinate and reference coordinate, in that a user is allowed to select the change rate.

Moreover, in the invention in the aforementioned aspects, it is preferred to perform the control by determining the gain depending upon the value of a coordinate between a second reference coordinate on the gain axis and a third reference coordinate on the gain axis having a larger value than the second reference coordinate; decreasing the gain corresponding to a coordinate having a value equal to or less than the second reference coordinate; and increasing the gain corresponding to a coordinate having a value equal to or greater than the third reference coordinate, in that a time-gain curve can be set as drawn by a user on the surface of the tablet pointer and the time-gain curve can be finely adjusted.

Furthermore, in the invention in the aforementioned aspects, it is preferred to perform the control by selectively switching among a mode in which the gain is determined depending upon the value of a coordinate on the gain axis; a mode in which the gain is increased corresponding to a coordinate on one side with respect to a reference coordinate on the gain axis, and the gain is decreased corresponding to a coordinate on the other side; and a mode in which the gain is determined depending upon the value of a coordinate between a second reference coordinate on the gain axis and a third reference coordinate on the gain axis having a larger value than the second reference coordinate, the gain is decreased corresponding to a coordinate having a value equal to or less than the second reference coordinate, and the gain is increased corresponding to a coordinate having a value equal to or greater than the third reference coordinate, in that the user is allowed select a desirable setting mode.

As described above in detail, the present invention can provide a method and apparatus for performing precise time-gain control using a small manual setting device, a medium recorded with a program for causing a computer to implement such a time-gain controlling function, and an ultrasonic imaging apparatus comprising such a time-gain controlling apparatus.

Further objects and advantages of the present invention will be apparent from the following description of the preferred embodiments of the invention as illustrated in the accompanying drawings.

BRIEF DESCRIPTION OF THE DRAWINGS

FIG. 1 is a block diagram of an apparatus in accordance with one embodiment of the present invention.

FIG. 2 is a block diagram of a transceiver section in the apparatus shown in FIG. 1.

FIG. 6 is a block diagram of a B-mode processing section in the apparatus shown in FIG. 1.

FIG. 7 is a block diagram of a Doppler processing section in the apparatus shown in FIG. 1.

FIG. 8 is a block diagram of an image processing section in the apparatus shown in FIG. 1.

FIG. 25 is a flow chart of the operation of the apparatus in accordance with one embodiment of the present invention.

DETAILED DESCRIPTION OF THE INVENTION

Figure 3:
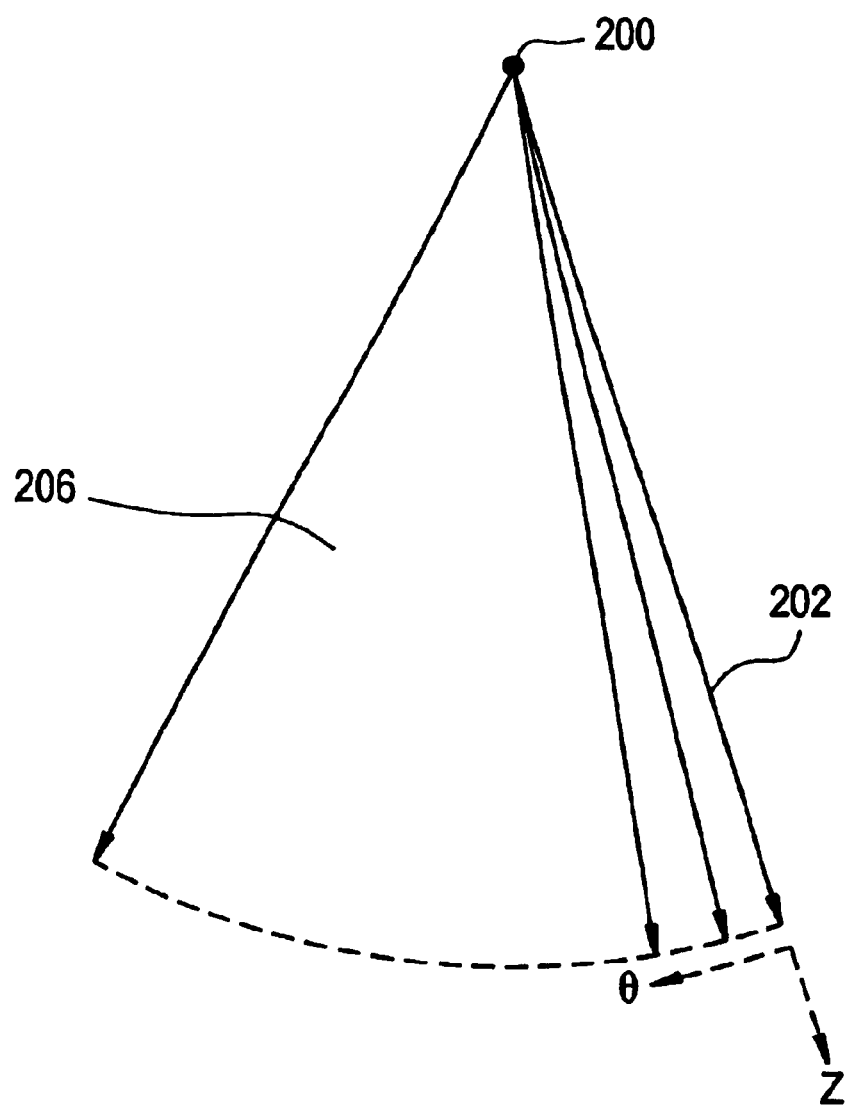
FIG. 3 is a conceptual diagram of a scan by the transceiver section shown in FIG. 2.

Several embodiments of the present invention will now be described in detail with reference to the accompanying drawings. It should be noted that the present invention is not limited to the embodiments. FIG. 1 shows a block diagram of an ultrasonic imaging apparatus, which is an embodiment of the present invention. The configuration of the apparatus represents an embodiment of the apparatus in accordance with the present invention. The operation of the apparatus represents an embodiment of the method in accordance with the present invention.

As shown in FIG. 1, the present apparatus has an ultrasonic probe 2. The ultrasonic probe 2 has an array of ultrasonic transducers (not shown). The individual ultrasonic transducers are made from a piezoelectric material such as PZT (lead zirconate titanate [Pb—Zr—Ti]) ceramic. The ultrasonic probe 2 is used abutted against an object 4 by a user.

The ultrasonic probe 2 is connected to a transceiver section 6. The transceiver section 6 supplies driving signals to the ultrasonic probe 2 to transmit ultrasound. It also receives echo signals caught by the ultrasonic probe 2. A portion consisting of the ultrasonic probe 2 and the transceiver section 6 is an embodiment of the ultrasound transmitting means of the present invention. It is also an embodiment of the echo receiving means of the present invention.

FIG. 2 shows a block diagram of the transceiver section 6. As shown, the transceiver section 6 has a transmission timing generating unit 602. The transmission timing generating unit 602 periodically generates a transmission timing signal, and inputs the signal to a transmission beamformer 604. The periodic cycle for the transmission timing signal is controlled by a control section 18, which will be described later.

The transmission beamformer 604 is for performing beamforming for the transmission, involving generating a beamforming signal for forming an ultrasonic beam in a certain direction based on the transmission timing signal. The beamforming signal consists of a plurality of driving signals that are given respective time differences corresponding to the direction. The beamforming is controlled by the control section 18, which will be described later. The transmission beamformer 604 inputs the transmission beamforming signal to a transmission/reception switching unit 606.

The transmission/reception switching unit 606 inputs the beamforming signal to the ultrasonic transducer array. A plurality of ultrasonic transducers that constitute a transmission aperture in the ultrasonic transducer array generate ultrasound having respective phase differences corresponding to the time differences in the driving signals. By wavefront synthesis of the ultrasound, a ultrasonic beam is formed along an acoustic line in a certain direction.

The transmission/reception switching unit 606 is connected with a reception beamformer 610. The transmission/reception switching unit 606 inputs the echo signals caught by a reception aperture in the ultrasonic transducer array to the reception beamformer 610. The reception beamformer 610 is for performing beamforming for the reception corresponding to an acoustic line for the transmission, involving imparting time differences to a plurality of received echoes to adjust their phases, and then adding the echoes to form an echo received signal along an acoustic line in a certain direction. The reception beamforming is controlled by the control section 18, which will be described later.

The transmission of the ultrasonic beam is repeated at predefined time intervals according to the transmission timing signal generated by the transmission timing generating unit 602. Synchronously with the timing, the transmission beamformer 604 and the reception beamformer 610 change the direction of the acoustic line by a predefined amount. Thus, the interior of the object 4 is sequentially scanned by the acoustic line.

The transceiver section 6 having such a configuration performs a scan as exemplarily shown in FIG. 3. Specifically, a fan-shaped two-dimensional region 206 is scanned in the θ-direction by an acoustic line 202 extending from an emission point 200 in the z-direction, and a so-called sector scan is carried out.

Figure 4:
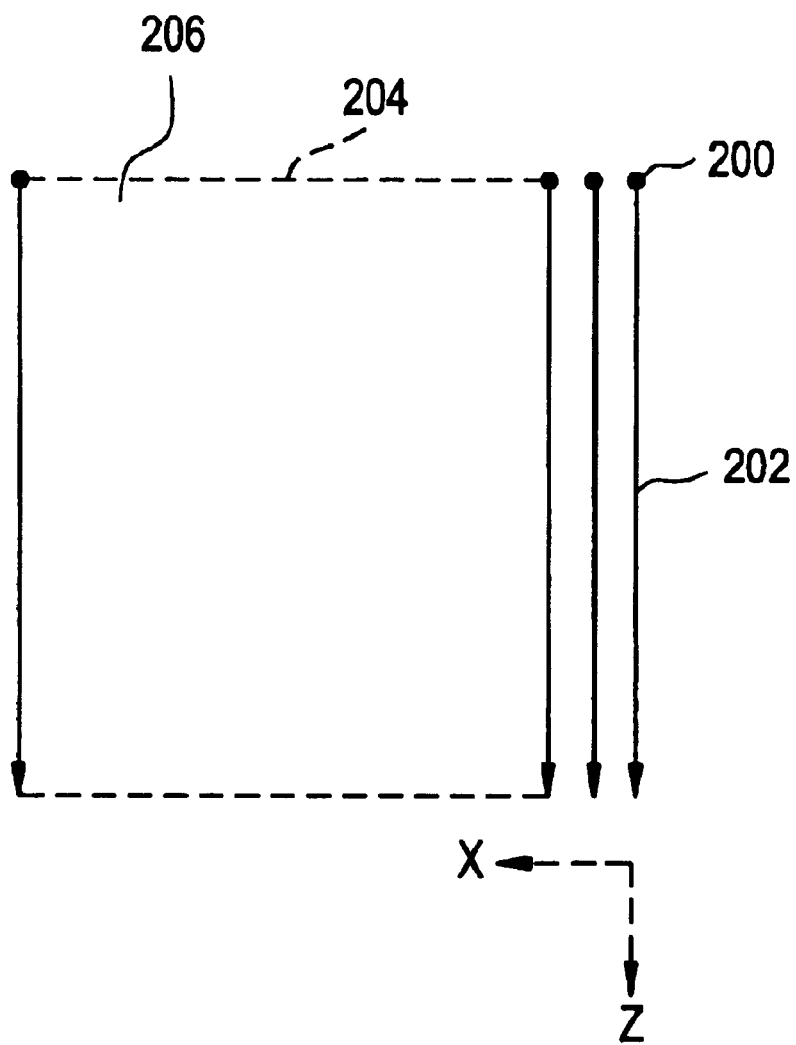
FIG. 4 is a conceptual diagram of a scan by the transceiver section shown in FIG. 2.

When the transmission and reception apertures are formed using part of the ultrasonic transducer array, a scan as exemplarily shown in FIG. 4 can be performed by sequentially shifting the apertures along the array. Specifically, a rectangular two-dimensional region 206 is scanned in the x-direction by translating an acoustic line 202, which emanates from an emission point 200 in the z-direction, along a linear trajectory 204, and a so-called linear scan is carried out.

Figure 5:
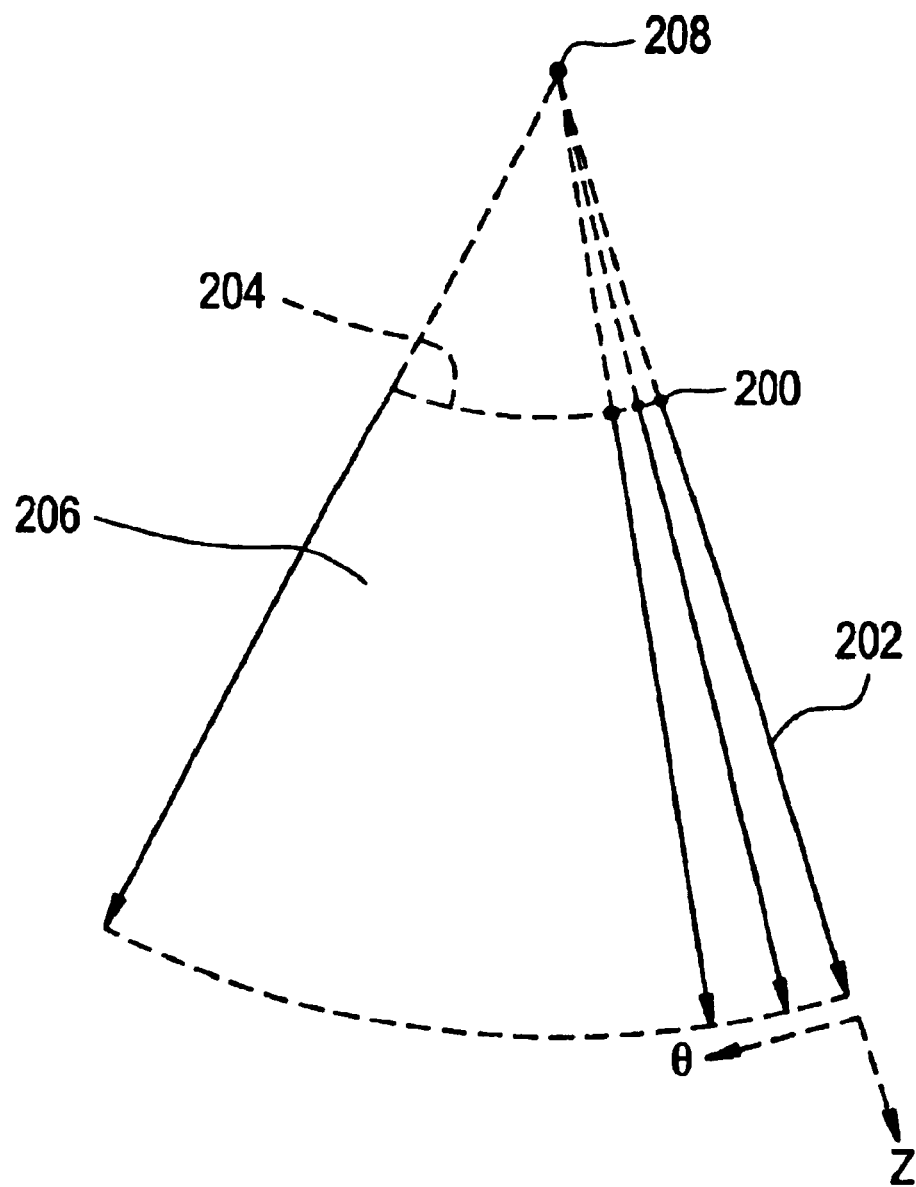
FIG. 5 is a conceptual diagram of a scan by the transceiver section shown in FIG. 2.

It will be easily recognized that when the ultrasonic transducer array is a so-called convex array, which is formed along an arc protruding in the direction of ultrasound transmission, a partial fan-shaped two-dimensional region 206 can be scanned in the θ-direction by performing an acoustic line scan similar to that for the linear scan and moving an emission point 200 of an acoustic line 202 along an arc-like trajectory 204, as exemplarily shown in FIG. 5, and a so-called convex scan is carried out.

The transceiver section 6 is connected to a B-mode processing section 10 and a Doppler processing section 12. The echo received signal for each acoustic line output from the transceiver section 6 is input to the B-mode processing section 10 and the Doppler processing section 12.

The B-mode processing section 10 is for generating B-mode image data. The B-mode processing section 10 comprises a logarithmic amplifying unit 102, an envelope detecting unit 104, and a TGC (time-gain control) unit 106, as shown in FIG. 6.

The B-mode processing section 10 logarithmically amplifies the echo received signal at the logarithmic amplifying unit 102; detects its envelope at the envelope detecting unit 104; performs time-gain control at the TGC unit 106 to obtain a signal indicating the intensity of the echo at each reflection point on an acoustic line, i.e., an A-scope signal; and generates B-mode image data using the amplitude of the A-scope signal at each instant as the brightness. A time-gain curve for use by the TGC unit 106 to perform the time-gain control is supplied by the control section 18.

The Doppler processing section 12 is for generating Doppler image data. The Doppler image data includes flow velocity data, variance data and power data, which will be described below.

As shown in FIG. 7, the Doppler processing section 12 comprises a quadrature detecting unit 120, an MTI (moving target indication) filter 122, an autocorrelation calculating unit 124, an average flow velocity calculating unit 126, a variance calculating unit 128 and a power calculating unit 130.

The Doppler processing section 12 quadrature-detects the echo received signal at the quadrature detecting unit 120, and MTI-processes the signal at the MTI filter 122 to obtain the Doppler shift in the echo signal. Moreover, it also performs an autocorrelation calculation on the output signal from the MTI filter 122 at the autocorrelation calculating unit 124; calculates an average flow velocity V from the result of the autocorrelation calculation at the average flow velocity calculating unit 126; calculates a variance T of the flow velocity from the result of the autocorrelation calculation at the variance calculating unit 128; and calculates a power PW of the Doppler signal from the result of the autocorrelation calculation at the power calculating unit 130. The average flow velocity will sometimes be referred to simply as the flow velocity hereinbelow. Moreover, the variance of the flow velocity will sometimes be referred to simply as the variance, and the power of the Doppler signal simply as the power hereinbelow.

The Doppler processing section 12 gives data representing the flow velocity V, variance T and power PW of an echo source moving inside the object 4 for each acoustic line. The data represents the flow velocity, variance and power at each point (pixel) on an acoustic line. The flow velocity is obtained as a component in an acoustic line direction, and a direction approaching the ultrasonic probe 2 and a direction going away from the ultrasonic probe 2 are distinguished.

The B-mode processing section 10 and the Doppler processing section 12 are connected to an image processing section 14. The image processing section 14 produces a B-mode image and a Doppler image based on respective data supplied from the B-mode processing section 10 and the Doppler processing section 12. The image processing section 14 is an embodiment of the image producing means of the present invention.

The image processing section 14 comprises a central processing unit (CPU) 140, as shown in FIG. 8. The CPU 140 is connected with a main memory 144, an external memory 146, a control section interface 148, an input data memory 152, a digital scan converter (DSC) 154, an image memory 156 and a display memory 158 via a bus 142.

The external memory 146 stores programs executed by the CPU 140. It also stores several kinds of data for use by the CPU 140 in executing the programs.

The CPU 140 carries out predefined image processing by loading a program from the external memory 146 into the main memory 144 for execution. The CPU 140 communicates control signals with the control section 18, which will be described later, via the control section interface 148 in the course of the program execution.

The B-mode image data and the Doppler image data for each acoustic line supplied from the B-mode processing section 10 and the Doppler processing section 12 are stored in the input data memory 152. The data in the input data memory 152 are scan-converted at the DSC 154 and stored in the image memory 156. The data in the image memory 156 are output to a display section 16 via the display memory 158.

The image processing section 14 is connected with a display section 16. The display section 16 is an embodiment of the display means of the present invention. The display section 16 is supplied with image data from the image processing section 14, and displays an image based on the image data. The display section 16 comprises a graphic display or the like capable of displaying a color image.

The transceiver section 6, B-mode processing section 10, Doppler processing section 12, image processing section 14 and display section 16 are connected with the control section 18. The control section 18 supplies control signals to these sections for controlling their operation. The control section 18 is supplied with several kinds of notification signals from the controlled sections. The B-mode operation and the Doppler mode operation are executed under control of the control section 18.

The control section 18 is connected with an operating section 20. The operating section 20 is operated by the user, and the section 20 inputs appropriate instructions and information to the control section 18. The operating section 20 comprises, for example, a keyboard, pointing device and other operating devices. The operating section 20 contains a manual setting device for time-gain control, which will be described later.

Figure 9:
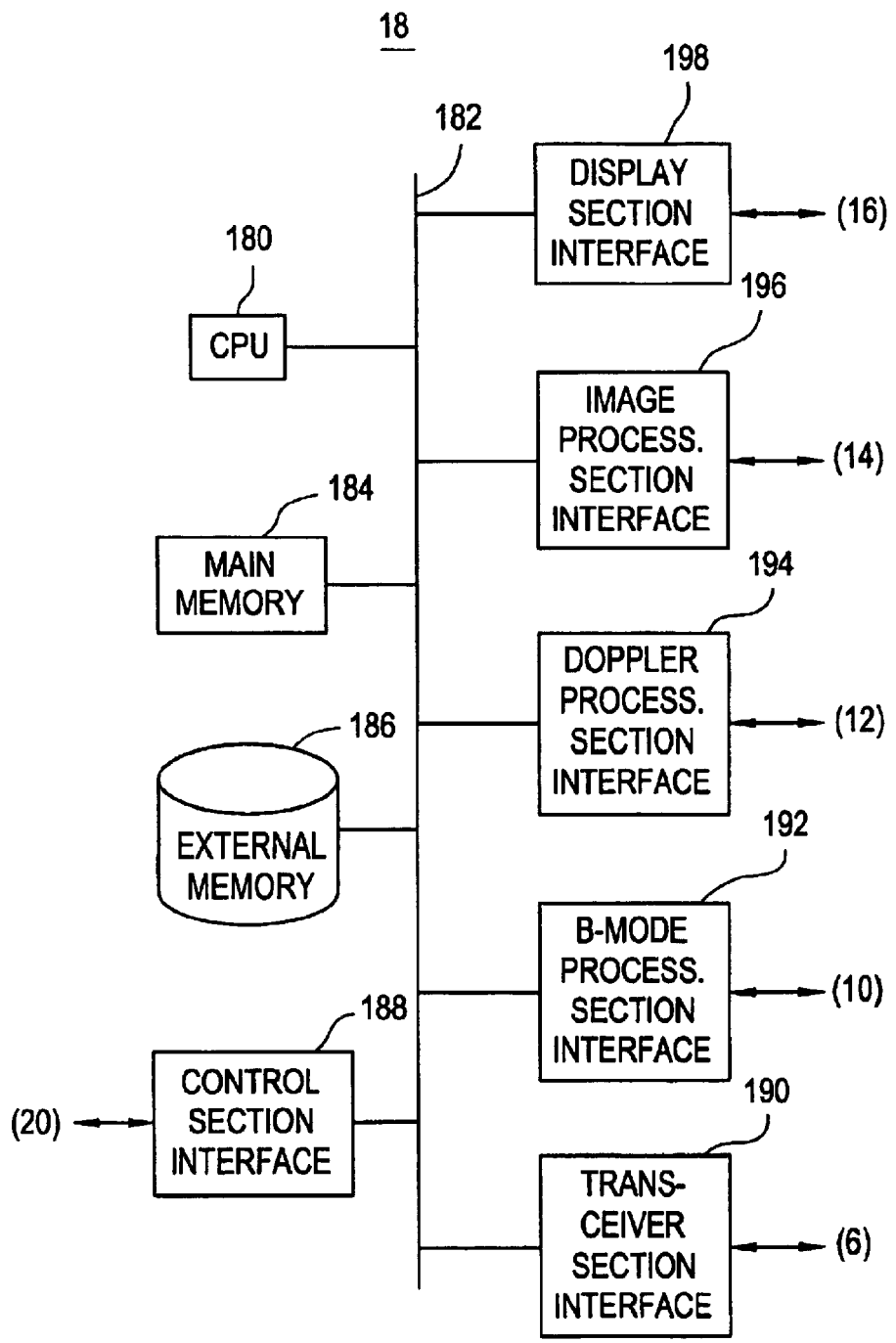
FIG. 9 is a block diagram of a control section in the apparatus shown in FIG. 1.

The control section 18 comprises a CPU 180, as shown in FIG. 9. The CPU 180 is connected with a main memory 184, an external memory 186, an operating section interface 188, a transceiver section interface 190, a B-mode processing section interface 192, a Doppler processing section interface 194, an image processing section interface 196 and a display section interface 198 via a bus 182.

The external memory 186 stores programs executed by the CPU 180. It also stores several kinds of data for use by the CPU 180 in executing the programs.

The CPU 180 carries out predefined control by loading a program from the external memory 186 into the main memory 184 for execution. The program stored in the external memory 186 also causes the CPU 180 to implement time-gain adjusting control, which will be described later. The CPU 180 communicates control signals with the transceiver section 6 via the transceiver section interface 190 in the course of the program execution.

Now the imaging operation of the present apparatus will be described. The user abuts the ultrasonic probe 2 against a desired portion on the object 4, and operates the operating section 20 for performing imaging operation in, for example, a B-mode and a Doppler mode combined. Thus, B-mode imaging and Doppler mode imaging are performed in a time-sharing manner under control of the control section 18. Specifically, a combined scan in the B-mode and the Doppler mode is performed at a rate of, for example, a scan in the B-mode performed once every so many scans in the Doppler mode.

In the B-mode, the transceiver section 6 scans the interior of the object 4 sequentially for every acoustic line and receives an echo each time through the ultrasonic probe 2. The B-mode processing section 10 logarithmically amplifies the echo received signal supplied from the transceiver section 6 at the logarithmic amplifying unit 102; envelope-detects the signal at the envelope detecting unit 104; performs TGC at the TGC unit 106 to determine an A-scope signal; and generates B-mode image data for each acoustic line based on the A-scope signal.

The image processing section 14 stores the B-mode image data for each acoustic line supplied from the B-mode processing section 10 in the input data memory 152. Thus, an acoustic line data space for the B-mode image data is formed in the input data memory 152.

In the Doppler mode, the transceiver section 6 scans the interior of the object 4 sequentially for every acoustic line and receives an echo each time through the ultrasonic probe 2. In the scanning, the ultrasound transmission and echo reception are performed a plurality of times per acoustic line.

The Doppler processing section 12 quadrature-detects the echo received signal at the quadrature detecting unit 120; MTI-processes the signal at the MTI filter 122; calculates an autocorrelation at the autocorrelation calculating unit 124; calculates a flow velocity V from the result of the autocorrelation calculation at the flow velocity calculating unit 126; calculates a variance T at the variance calculating unit 128; and calculates a power PW at the power calculating unit 130. These calculated values constitute data representing the velocity, variance and power of an echo source for each acoustic line and for each pixel.

The image processing section 14 stores the Doppler image data for each acoustic line and for each pixel supplied from the Doppler processing section 12 into the input data memory 152. Thus, an acoustic line data space is formed for the Doppler image data in the input data memory 152.

The CPU 140 scan-converts the B-mode image data and the Doppler image data in the input data memory 152 at the DSC 154, and writes the scan-converted data into the image memory 156.

In writing the data, the Doppler image data are written as flow velocity distribution image data in which the flow velocity V and the variance T are combined, power Doppler image data employing the power PW or power Doppler image data with variance in which the power PW and the variance T are combined, and variance image data employing the variance T.

The CPU 140 writes the B-mode image data and the Doppler image data into separate regions. Then, images based on the B-mode image data and the Doppler image data are displayed on the display section 16.

A B-mode image represents a cross-sectional image of an internal tissue in an acoustic line scan plane. A flow velocity distribution image of color Doppler images represents a two-dimensional distribution of the flow velocity of the echo source. In this image, the display color is differentiated depending upon the flow direction; the brightness of the display color is differentiated depending upon the flow velocity; and the purity of the display color is varied by increasing the amount of a certain color to be mixed depending upon the variance.

A power Doppler image represents a two-dimensional distribution of the power of the Doppler signal. The image indicates the location of a moving echo source. The brightness of the display color for the image corresponds to the power. If the variance is combined with the power, the purity of the display color is varied by increasing the amount of a certain color to be mixed depending upon the variance.

A variance image represents a two-dimensional distribution of the variance value. This image also indicates the location of a moving echo source. The brightness of the display color corresponds to the magnitude of the variance.

In displaying these images on the display section 16, each image is superimposed on the B-mode image at the display memory 158 to display a composite image on the display section 16. Thus, a color Doppler image that distinctly indicates a position relationship relative to the internal tissue can be observed.

Figure 10:
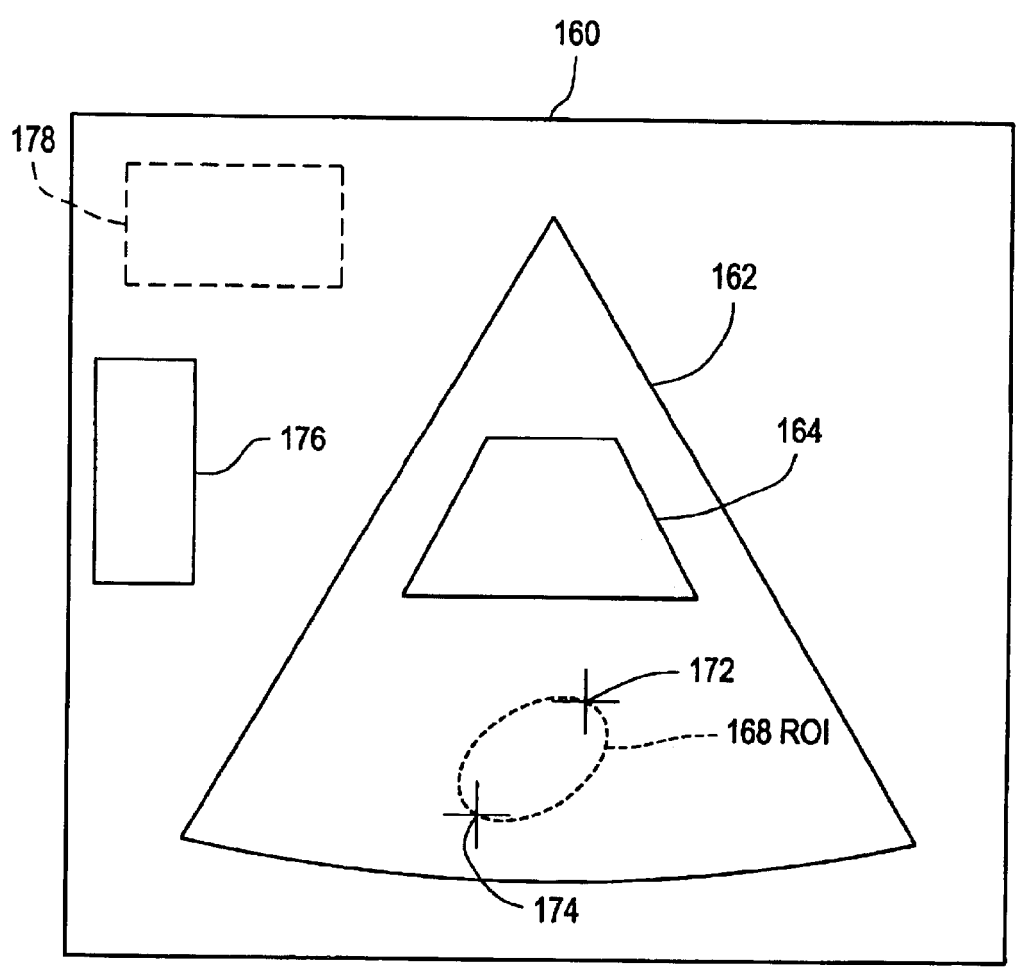
FIG. 10 is a schematic diagram showing an example of a screen on a display section in the apparatus shown in FIG. 1.

FIG. 10 schematically shows an example of a screen displaying such images. As shown, a B-mode image 162 is displayed on a screen 160, which image is captured by a sector scan. Over the B-mode image 162 is displayed a color Doppler image 164. It should be noted that the color Doppler image 164 is represented by a boundary of a display area.

A region of interest (ROI) 168 is defined in the B-mode image 162, and measurement cursors 172 and 174 are displayed at two positions on the outline of the ROI 168. The ROI 168 can be freely drawn by the user employing the pointing device. Similarly, the measurement cursors 172 and 174 can be freely moved by the user via the pointing device.

In the marginal space of the screen 160 are displayed a gray scale 176 that measures the tone of the B-mode image 162, and a user comment 178.

Figure 11:
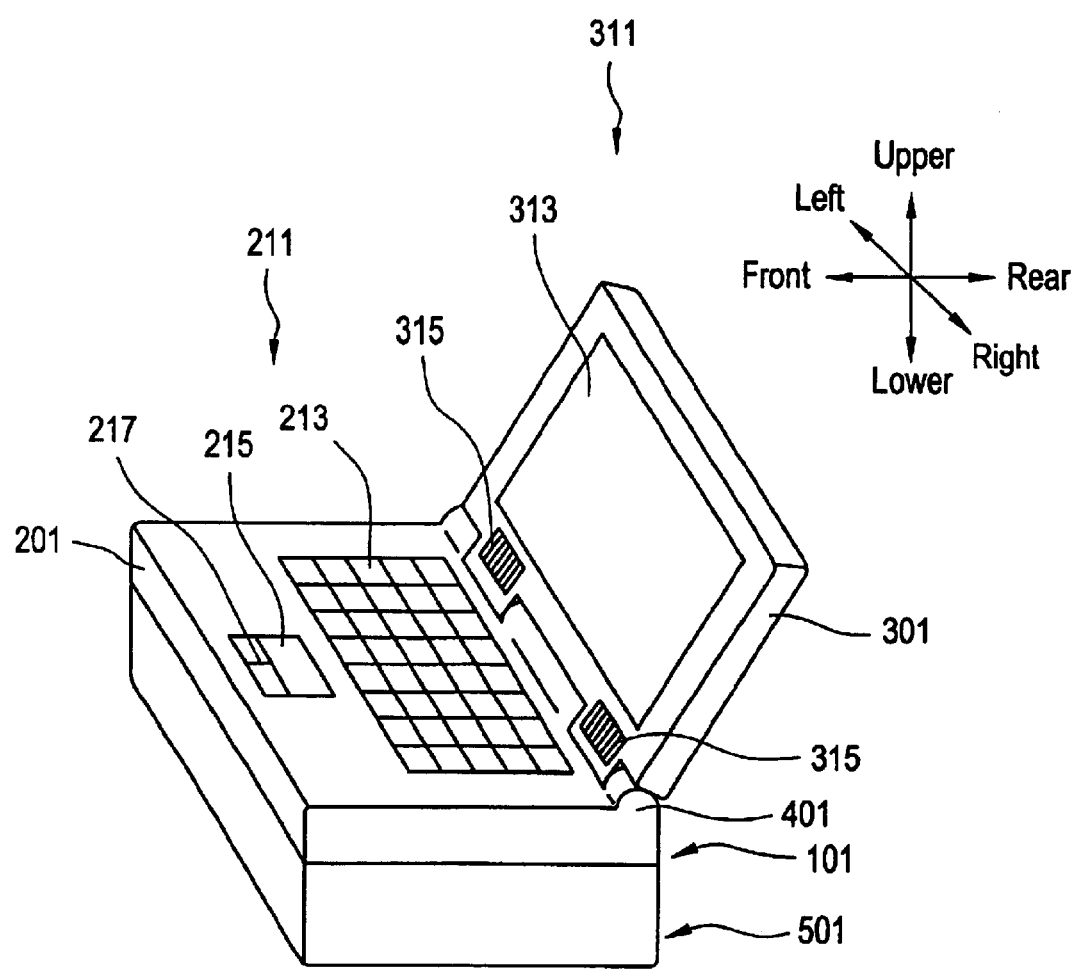
FIG. 11 is a schematic diagram showing the physical configuration of an apparatus in accordance with one embodiment of the present invention.

FIG. 11 schematically shows the physical configuration of a body of the ultrasonic imaging apparatus. As shown, the present apparatus is comprised of an imaging apparatus 101 and a support apparatus 501. The imaging apparatus 101 has basic ultrasonic imaging functions among the functions of the present apparatus. The support apparatus 501 has functions for supporting the imaging apparatus 101 to extend the functions of the imaging apparatus 101.

With respect to the present apparatus, front and rear, right and left, and upper and lower directions are defined by arrows shown in FIG. 11. The imaging apparatus 101 is constructed by joining a generally box-shaped body 201 with a generally planar panel 301 via a hinge 401. The hinge 401 is provided between the upper end portion of the rear end of the body 201 and the lower end portion of the panel 301.

The panel 301 can rotate relative to the body 201 around the hinge 401. The hinge 401 has a moderate frictional resistance to allow the panel 301 to be fixed at an arbitrary rotation angle.

Figure 12:
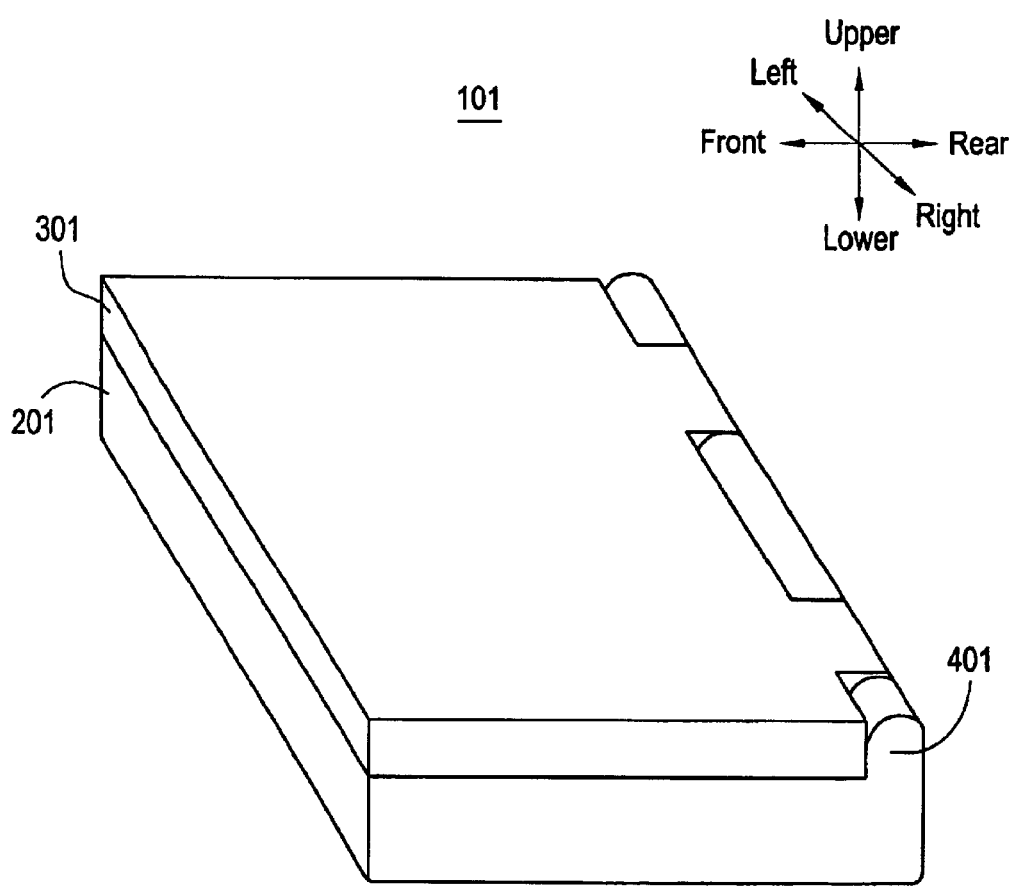
FIG. 12 is a schematic diagram showing part of the physical configuration of an apparatus in accordance with one embodiment of the present invention.

When the panel 301 is rotated counterclockwise to the maximum degree in the drawing, the panel 301 can be turned down on the upper surface of the body 201 as shown in FIG. 12. This condition will be sometimes referred to as the folded condition of the imaging apparatus 101 hereinbelow. A rear surface of the body 201, which is hidden in the drawing, is provided with a connector for connecting an ultrasonic probe.

The upper surface of the body 201 is configured as an operating section 211 of the present apparatus. The operating section 211 corresponds to the operating section 20 shown in FIG. 1. The operating section 211 has a keyboard 213 and a tablet pointer 215. The tablet pointer 215 is an embodiment of the tablet pointer of the present invention. The tablet pointer 215 is provided with a pair of click buttons 217.

The tablet pointer 215 has a structure and function common to those used as a pointing device in notebook PC's (personal computers) and the like. Specifically, it has a surface which the user can touch with a fingertip or an appropriate dedicated tool such as a stylus, and generates two-dimensional coordinates of a position on the surface which the user touches. The generated two-dimensional coordinates are input to the control section 18. The user's fingertip, the dedicated tool or the like is an embodiment of the external object that touches the surface of the tablet pointer 215.

In the present apparatus, the tablet pointer 215 is employed not only as an ordinary pointing device, but also as an operating tool for the user to set a time-gain curve for the TGC. The setting of the time-gain curve using the tablet pointer 215 will be described later.

A front surface of the panel 301 is configured as a display section 311. The display section 311 corresponds to the display section 16 shown in FIG. 1. The display section 311 has an image display device 313 and a pair of sound output devices 315. For the image display device 313, a flat panel display, such as, for example, an LCD (liquid crystal display), is employed. For the sound output devices 315, speakers, for example, are employed.

The support apparatus 501 has a generally box-shaped outer shape. The upper surface of the support apparatus 501 has a shape adapted to the lower surface of the imaging apparatus 101. The imaging apparatus 101 is mounted over the support apparatus 501.

The imaging apparatus 101 is removable with respect to the support apparatus 501. Therefore, the imaging apparatus 101 can be removed from the support apparatus 501 and folded as shown in FIG. 12 for carrying.

The imaging apparatus 101 has a configuration such that it can perform basic ultrasonic imaging by itself. Thus, the ultrasonic imaging can be performed at a site to which the imaging apparatus 101 is carried. When the imaging apparatus 101 is used with the support apparatus 501 attached, precise imaging and so forth can be performed by employing the extended functions of the support apparatus 501. The support apparatus 501 is stationarily installed in a scan room or the like, and when precise imaging is to be performed, the imaging apparatus 101 is used with the support apparatus 501 attached in the scan room.

Figure 13:
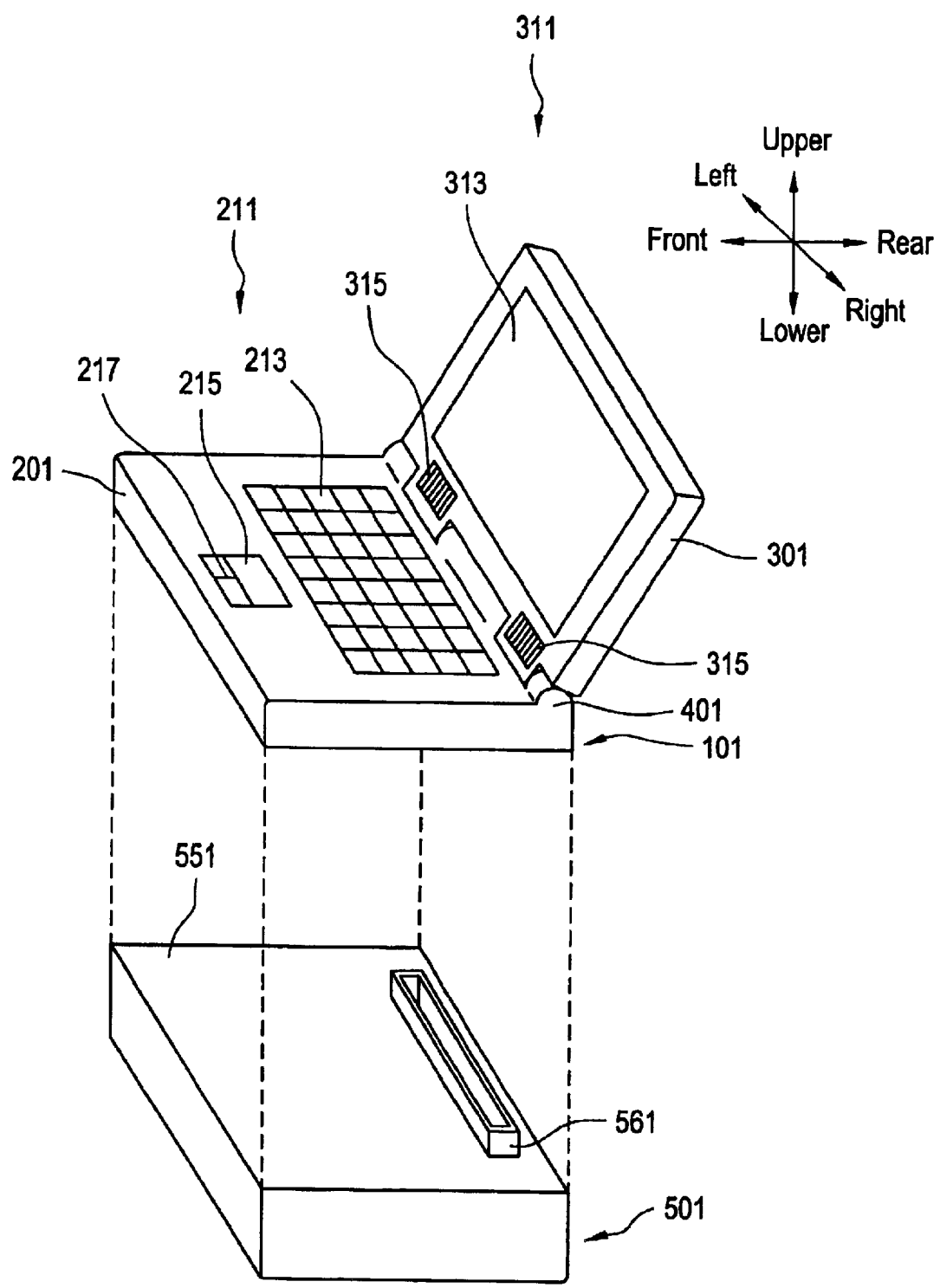
FIG. 13 is a schematic diagram showing the physical configuration of an apparatus in accordance with one embodiment of the present invention.

FIG. 13 shows the condition when the imaging apparatus 101 is removed from the support apparatus 501. As shown, the support apparatus 501 has a connector 561 on its upper surface, or a top portion 551. The connector 561 protrudes in the upper direction.

On the lower surface of the imaging apparatus 101 is provided a receptor 121 corresponding to the connector 561, which will be described below, and the connector 561 and the receptor 121 are electrically and mechanically joined when the imaging apparatus 101 is mounted over the support apparatus 501.

Figure 14:
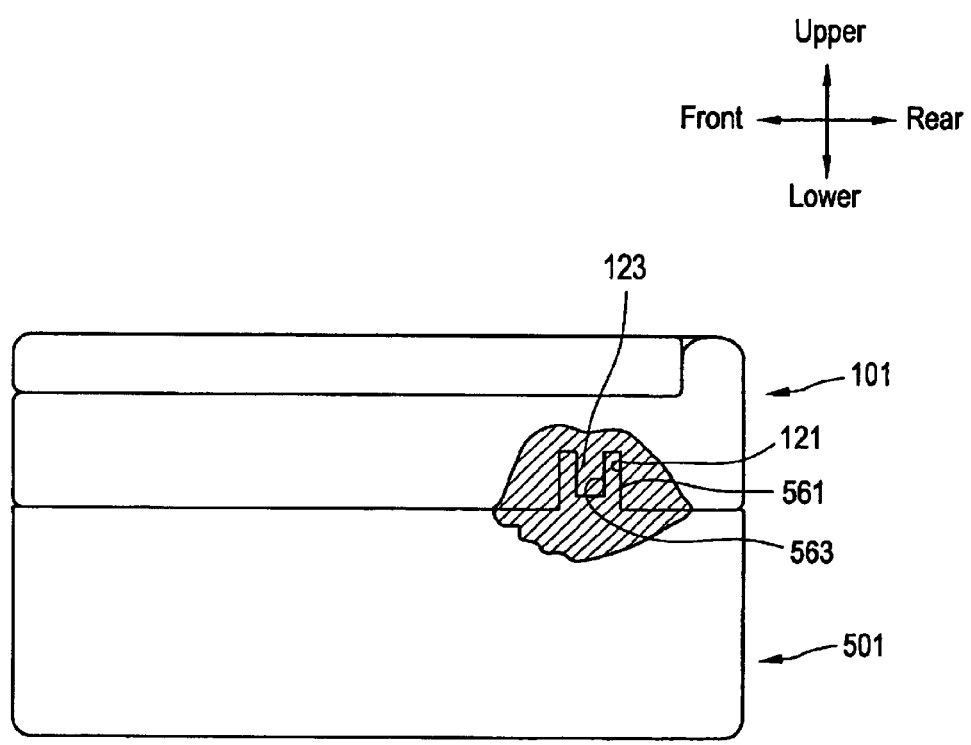
FIG. 14 is a schematic diagram showing the physical configuration of an apparatus in accordance with one embodiment of the present invention.

FIG. 14 schematically shows the joined condition of the connector 561 and the receptor 121. As shown, the receptor 121 is concave so as to receive the connector 561. The engagement between the receptor 121 and the connector 561 forms the mechanical joint of the imaging apparatus 101 and the support apparatus 501.

The connector 561 has a concave portion 563 extending inward from the tip to the base of the connector 561, and the receptor 121 has a protruding portion 123 protruding from the bottom to the entrance of the receptor 121. The protruding portion 123 can be fitted with the concave portion 563. The outer surface of the protruding portion 123 and the inner surface of the concave portion 563 are each provided with a plurality of electric contacts correspondingly, and contact between the corresponding electric contacts forms the electrical joint of the imaging apparatus 101 and the support apparatus 501.

Setting of a time-gain curve employing the tablet pointer 215 will now be described. The setting of a time-gain curve is carried out by manipulation of the tablet pointer 215 by the user and the operation of the CPU 180 in the control section 18 based upon the manipulation.

A portion consisting of the tablet pointer 215, control section 18 and TGC unit 106 is an embodiment of the time-gain controlling apparatus of the present invention. The configuration of the apparatus represents an embodiment of the apparatus in accordance with the present invention. The operation of the apparatus represents an embodiment of the method in accordance with the present invention.

Figure 15:
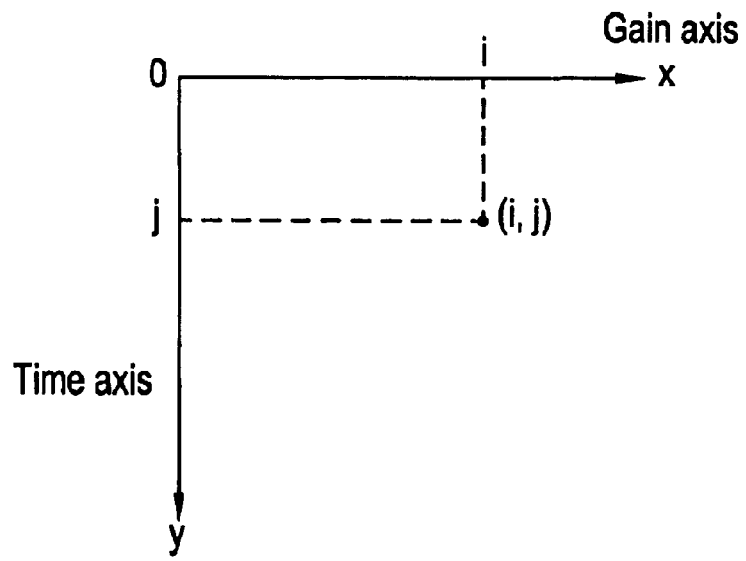
FIG. 15 shows a two-dimensional space in a tablet pointer.

FIG. 15 shows a two-dimensional coordinate space formed by the tablet pointer 215. The two-dimensional coordinate space has two coordinate axes x and y that are perpendicular to each other. When the user touches the surface of the tablet pointer 215 with the fingertip or the like, two-dimensional coordinates (i, j) of the position which the user touches are input to the CPU 180.

In a mode for setting a time-gain curve, the CPU 180 translates the x coordinate i of the input two-dimensional coordinates (i, j) as a coordinate on a gain axis, and y coordinate j as a coordinate on a time axis. Then, the CPU 180 determines a gain Gj at the position j on the time axis based on the coordinate i on the gain axis. The CPU 180 is an embodiment of the coordinate translating means of the present invention. It is also an embodiment of the controlling means of the present invention.

Figure 16:
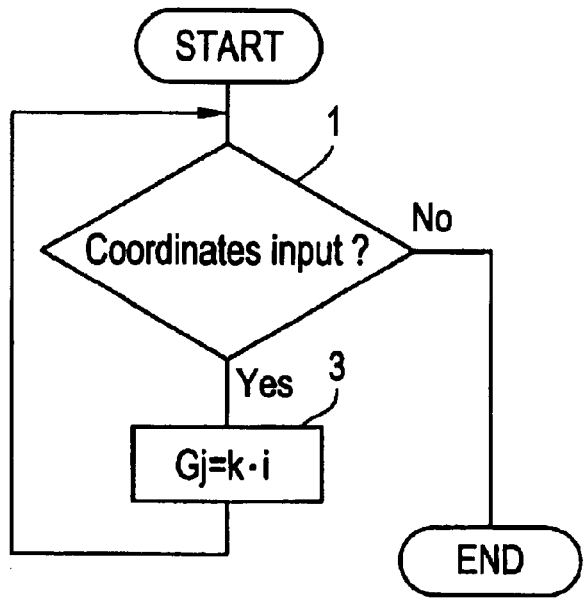
FIG. 16 is a flow chart of the operation of an apparatus in accordance with one embodiment of the present invention.

FIG. 16 shows a flow chart of an example of the time-gain controlling operation. The flow chart represents the operation of the CPU 180. Similarly, flow charts which will be shown later also represent the operation of the CPU 180. In Step 1 shown in FIG. 16, a decision is made as to whether coordinates are input. If coordinates are input, a gain at the position j on the time-axis is determined in Step 3 using the following equation:

[Equation 1]

$$Gj = k \cdot i, \quad (1)$$

wherein k is a constant.

Figure 17:
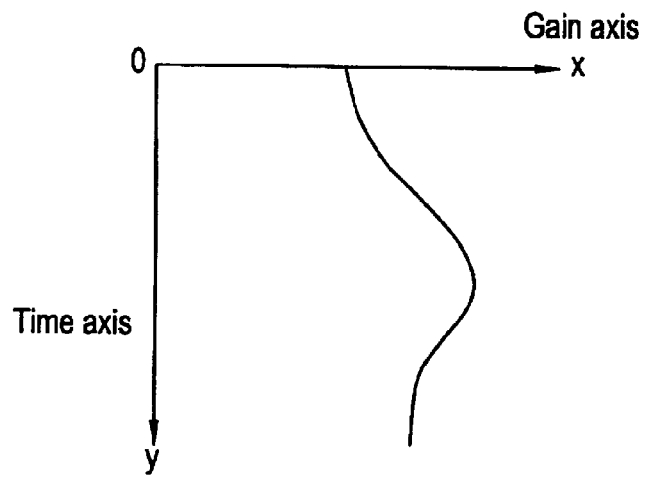
FIG. 17 shows a time-gain curve.

While the input of the coordinates is continued, such gain setting is continuously performed. Thus, if the user draws a desired time-gain curve on the surface of the tablet pointer 215 with the fingertip or the like, a time-gain curve as drawn is set, as exemplarily shown in FIG. 17.

The resolution of the time-gain curve in the gain axis direction and in the time axis direction are determined by the coordinate resolution of the tablet pointer 215. Since the tablet pointer generally has very high coordinate resolution, the time-gain curve has very high resolution both in the gain axis direction and in the time axis direction. Thus, a precise time-gain curve can be set.

Such setting of the time-gain curve, or time-gain control, is preferably performed while displaying a B-mode image being captured on the display section 16. Since the brightness distribution of a B-mode image in the depth direction is determined by the TGC based on the time-gain curve, the time-gain control can be performed as the user is verifying its effect by observing an actual image.

At the same time, the time-gain curve is preferably displayed on part of the display section 16, in that the setting of the time-gain curve is made easier. It should be noted that it is necessary to display the time-gain curve on the display section 16 when the setting of the time-gain curve is performed separately from imaging. This is true also in the operations which will be described later.

The time-gain curve may be rewritten any number of times until an image with desired brightness distribution is obtained. Thus, a time-gain curve as desired can be easily obtained. The preceding time-gain control will be sometimes referred as position-type time-gain control in this specification.

Figure 18:
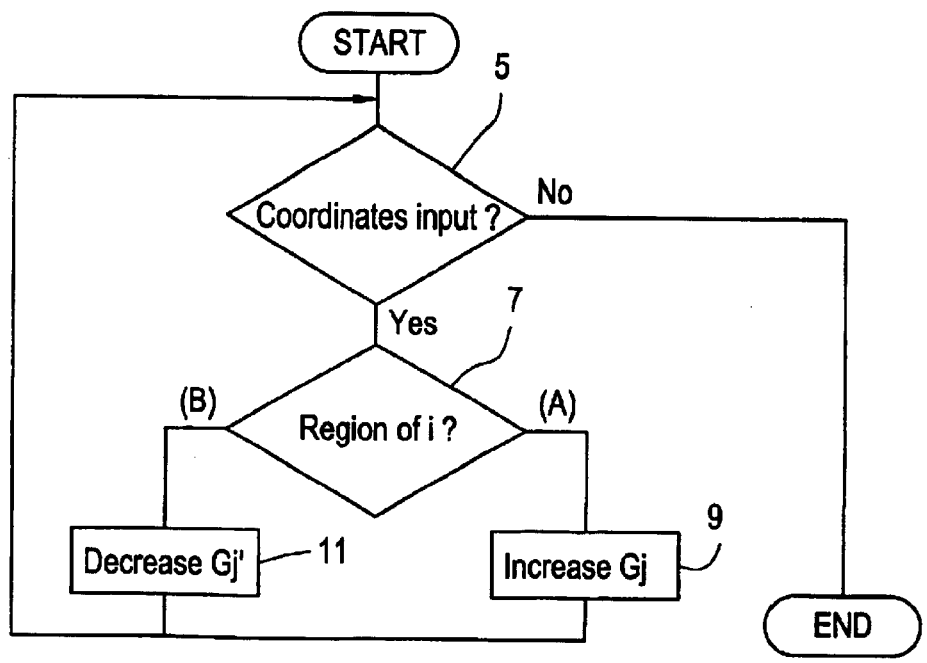
FIG. 18 is a flow chart of the operation of the apparatus in accordance with one embodiment of the present invention.

FIG. 18 shows a flow chart of another example of the time-gain control operation. As shown, in Step 5, a decision is made as to whether coordinates are input. If coordinates are input, a region to which a coordinate i belongs is determined.

Figure 19:
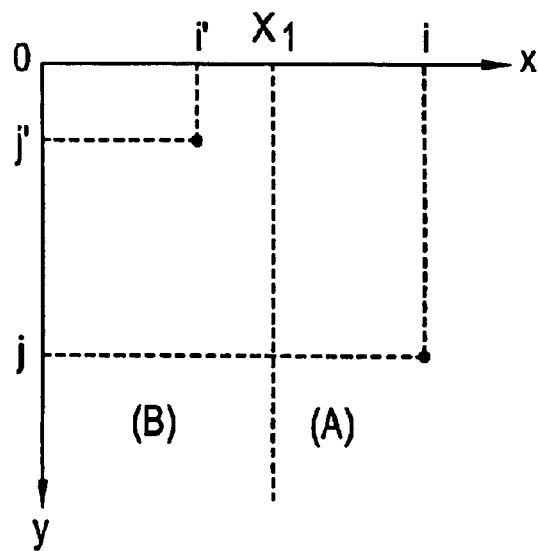
FIG. 19 shows a two-dimensional space in the tablet pointer.

The two-dimensional space is previously divided into two regions A and B bounded by a coordinate X1 on the x-axis, as exemplarily shown in FIG. 19. It should be noted that such division is logical division and this does not mean that the surface of the tablet pointer 215 is physically divided. The coordinate X1 is an embodiment of the reference coordinate of the present invention.

The coordinate X1 is, for example, a coordinate of the center of the x-axis. The region A is a region to which a coordinate having a value larger than the coordinate X1 belongs. The region B is a region to which a coordinate having a value smaller than the coordinate X1 belongs.

If the coordinates of the position which the user touches with the fingertip or the like are (i, j), the coordinates belong to the region A. In this case, the gain Gj is increased in Step 9. While the input of the coordinates (i, j) is continued, this operation is continued.

Figure 20:
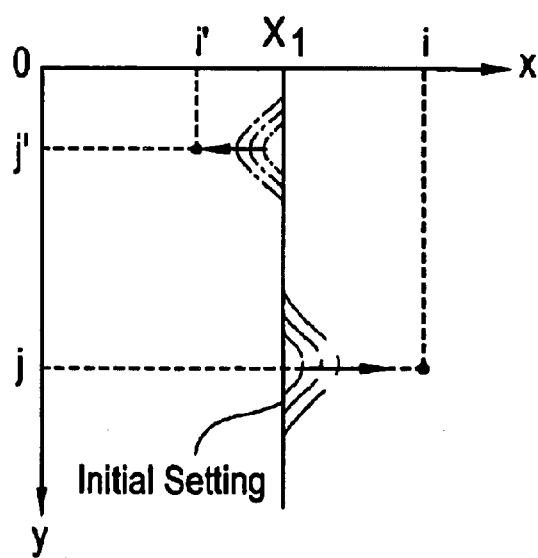
FIG. 20 shows a time-gain curve.

Thus, as exemplarily shown in FIG. 20, the initial setting of the time gain indicated by a solid line has an increased gain centered on a portion corresponding to the y-coordinate j as indicated by a dot-dash line.

The increased portion of the gain has a spread in the time axis direction. The width of the spread increases with an increase in the gain. The gain distributes within the width of the spread to have a peak at the center j. The distribution curve is, for example, a Gaussian distribution curve; however, it is not limited to the Gaussian distribution curve but may be any appropriate distribution curve.

If the coordinates of the position which the user touches with the fingertip or the like are (i', j'), the coordinates belong to the region B. In this case, the gain Gj' is decreased in Step 11. While the input of the coordinates (i', j') is continued, this operation is continued.

Thus, as exemplarily shown in FIG. 20, the initial setting of the time gain indicated by the solid line has a decreased gain centered on a portion corresponding to the y-coordinate j' as indicated by a dot-dash line.

The decreased portion of the gain also has a spread in the time axis direction. The width of the spread increases with a decrease in the gain. The spread is allowed to affect other portions at which the gain has been already adjusted. The gain distributes within the width of the spread to have a peak at the center j'. The distribution curve is, for example, a Gaussian distribution curve; however, it is not limited to the Gaussian distribution curve but may be any appropriate distribution curve.

Such time-gain control is also preferably performed while displaying an image on the display section 16.

A desired position in the time-gain curve that has been set can thus be arbitrarily changed. The change rate of the gain is a constant rate S regardless of the value of the coordinate i both in the increase and in the decrease, as exemplarily shown as "Rate 1" in FIG. 21. However, the rate is zero at the coordinate X1.

Figure 21:
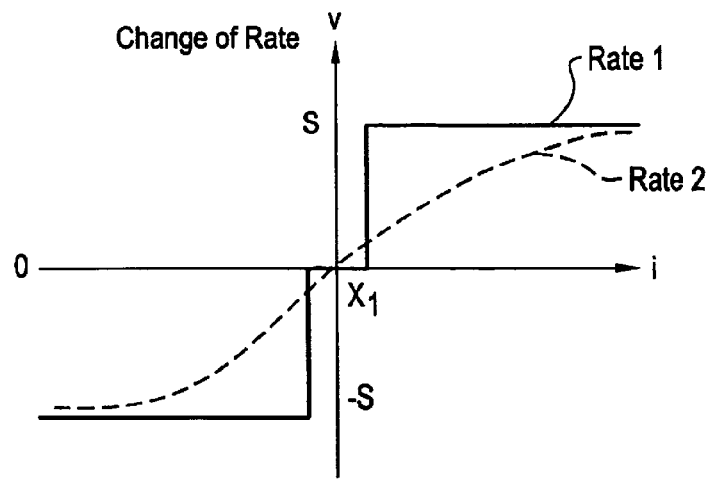
FIG. 21 is a graph showing the gain change rate.

The change rate of the gain may be varied depending upon the value of the coordinate i both in the increase and in the decrease, as exemplarily shown as "Rate 2" in FIG. 21. Specifically, when the difference from the coordinate X1 is small, the rate is decreased; and the rate increases with the increase in the difference. In this case, the user can vary the change rate of the gain by selecting the position on the surface of the tablet pointer 215 to be touched with the fingertip or the like, thereby making the adjustment of the gain curve easy.

The preceding time-gain control will be referred to as rate-type time-gain control in this specification. Moreover, the time-gain control by Rate 1 will be referred to as rate1-type time-gain control; and the time-gain control by Rate 2 as rate2-type time-gain control.

Figure 22:
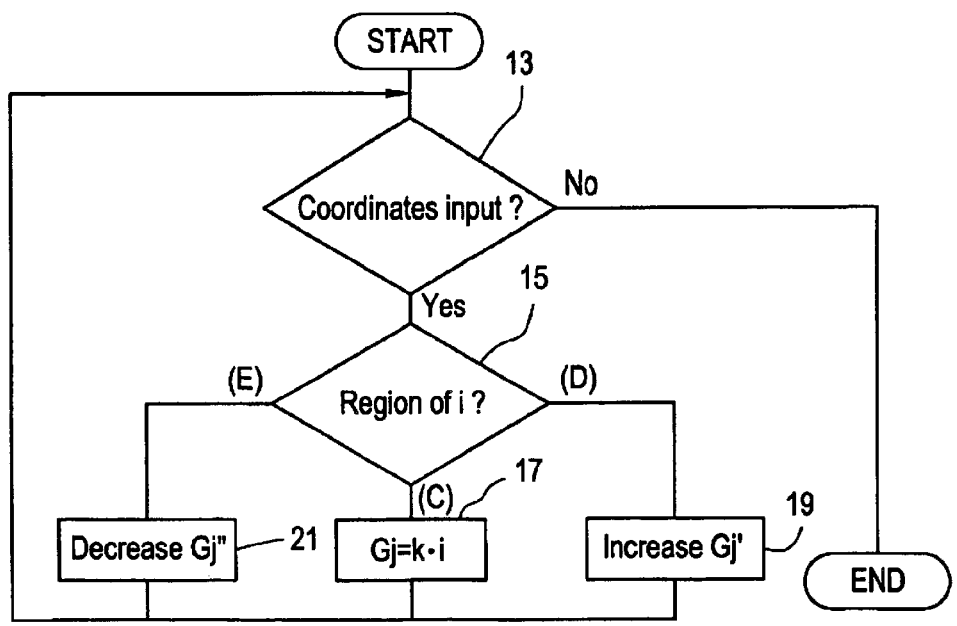
FIG. 22 is a flow chart of the operation of the apparatus in accordance with one embodiment of the present invention.

FIG. 22 shows a flow chart of still another example of the time-gain control operation. In this operation, the operations shown in FIGS. 16 and 18 are combined. As shown, a decision is made as to whether coordinates are input in Step 13. If coordinates are input, a region to which the coordinate i belongs is determined in Step 15.

Figure 23:
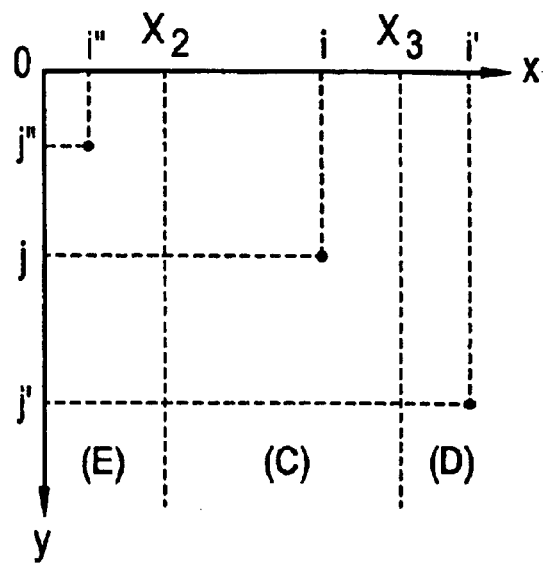
FIG. 23 shows a two-dimensional space in the tablet pointer.

The two-dimensional space is previously divided into three regions C, D and E bounded by coordinates X2 and X3 on the x-axis, as exemplarily shown in FIG. 23. It should be noted that such division is logical division and this does not mean that the surface of the tablet pointer 215 is physically divided. The coordinate X2 is an embodiment of the second reference coordinate of the present invention. The coordinate X3 is an embodiment of the third reference coordinate of the present invention.

The coordinate X2 is nearer to the origin than the center of the x-axis is. The coordinate X3 is farther from the origin than the center of the x-axis is. The region C is a region to which a coordinate having a value between the coordinates X2 and X3 belongs. The region D is a region to which a coordinate having a value greater than the coordinate X3 belongs. The region E is a region to which a coordinate having a value less than the coordinate X2 belongs.

If the coordinates of the position which the user touches with the fingertip or the like are (i, j), the coordinates belong to the region C. In this case, the gain Gj at the position j on the time axis is determined by Eq. (1) above in Step 17.

If the coordinates of the position which the user touches with the fingertip or the like are (i', j'), the coordinates belong to the region D. In this case, the gain Gj' is increased in Step 19. While the input of the coordinates (i', j') is continued, this operation is continued.

If the coordinates of the position which the user touches with the fingertip or the like are (i", j"), the coordinates belong to the region E. In this case, the gain Gj" is decreased in Step 21. While the input of the coordinates (i", j") is continued, this operation is continued.

Figure 24:
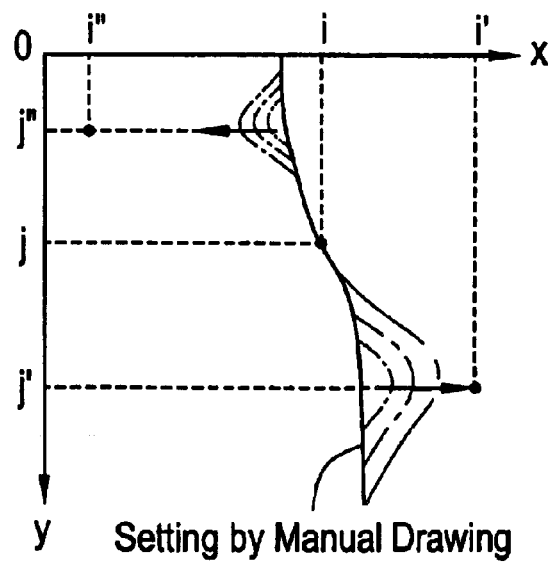
FIG. 24 shows a time-gain curve.

Thus, as exemplarily shown in FIG. 24, a time-gain curve indicated by a solid line can be set by manual drawing, and also the gain can be increased centered on a portion corresponding to the y-coordinate j' and decreased centered on a portion corresponding to the y-coordinate j", as indicated by a dot-dash line. In other words, setting of a time-gain curve by manual drawing and fine adjustment of the time-gain curve can be achieved. Again, such time-gain control is preferably performed while displaying an image on the display section 16.

The aforementioned time-gain control of the position type, rate 1 type, rate2 type and combination type may be appropriately switched according to a condition. A flow chart of the operation in this case is shown in FIG. 25. As shown, a control mode is determined in Step 23. If the position type is selected, the position-type time-gain control as shown in FIG. 16 is performed in Step 25; if the rate1 type is selected, the rate-type time-gain control as shown in FIG. 18 is performed at Rate 1 in Step 27; if the rate2 type is selected, the rate-type time-gain control as shown in FIG. 18 is performed at Rate 2 in Step 29; and if the combination type is selected, the combination-type time-gain control as shown in FIG. 22 is performed in Step 31.

As described above, a tablet pointer is employed for the manual setting by the user in the time-gain control in the present apparatus. The space needed for installing the tablet pointer is as small as 70 mm×50 mm×5 mm. The space is much smaller than the conventional manual setting section provided with a plurality of slide volumes. Moreover, in spite of such a small size, a precise time gain can be set in the gain axis direction and in the time axis direction, as described above.

Accordingly, such a tablet pointer is suitable for a TGC manual setting device for a portable ultrasonic imaging apparatus that is small and light, as exemplarily shown in FIG. 12. Moreover, it will be easily recognized that the tablet pointer is also suitable not only for such a small and light ultrasonic imaging apparatus but for a TGC manual setting device in a medium or large ultrasonic imaging apparatus.

While the present invention has been described with reference to an example of receiving ultrasonic echoes, the time-gain control is not limited to the ultrasonic echoes but may be generally applied to reception of echoes of other types of waves, such as electric waves. The technical scope of the present invention encompasses such applications.

A program for causing a computer to implement such a time-gain control function as described above is recorded on a recording medium in a computer-readable manner. For the recording medium, for example, any one of a magnetic recording medium, an optical recording medium, a magneto-optical recording medium and any other appropriate type of recording medium is employed. The recording medium may be a semiconductor storage medium. A storage medium is synonymous with a recording medium in the present specification.

While the present invention has been described with reference to preferred embodiments hereinabove, various changes or substitutions may be made on these embodiments by those ordinarily skilled in the art pertinent to the present invention without departing from the technical scope of the present invention. Therefore, the technical scope of the present invention encompasses not only those embodiments described above but all the embodiments that fall within the scope of the appended claims.

Many widely different embodiments of the invention may be configured without departing from the spirit and the scope of the present invention. It should be understood that the present invention is not limited to the specific embodiments described in the specification, except as defined in the appended claims.

What is claimed is:

1. A time gain controlling method for controlling a time gain for echo reception, comprising the steps of:
defining one of two dimensional coordinates of a position on a surface of a table pointer by an external object touching said surface and being sensed electrically to define said position as a coordinate on a time axis, and defining electrically the other of said two dimensional coordinates as a coordinate on a gain axis; and
controlling time gain based on said two dimensional coordinates, said controlling being performed by
determining said time gain depending on value of the coordinate on said gain axis;
increasing said time gain corresponding to a coordinate on one side with respect to a first reference coordinate on said gain axis; and
decreasing said time gain corresponding to a coordinate on the other side with respect to said first reference coordinate.

2. The method of claim 1, wherein rate of change of said increasing or decreasing of said time gain is constant.

3. The method of claim 2, wherein said rate of change of said time gain corresponds to a difference between said coordinate on said one side and said first reference coordinate.

4. The method of claim 1, wherein controlling is performed by the steps of:
    determining said time gain depending on value of a coordinate between a second reference coordinate on said gain axis and a third reference coordinate on said gain axis having a value larger than value of said second reference coordinate;
    decreasing said time gain corresponding to a coordinate having a value equal to or less than said second reference coordinate; and
    increasing said time gain corresponding to a coordinate having a value equal to or greater than value of said third reference coordinate.

5. The method of claim 1, wherein said controlling is performed by the steps of:
    selectively switching among:
        a mode in which said time gain is determined depending on value of a coordinate on said gain axis;
        a mode in which said time gain is increased corresponding to a coordinate on one side with respect to said first reference coordinate on said gain axis, and in which said time gain is decreased corresponding to a coordinate on the other side; and
        a mode in which said time gain is determined depending on value of a coordinate between a second reference coordinate on said gain axis and a third reference coordinate on said gain axis having a larger value than value of said second reference coordinate, and in which the time gain is decreased corresponding to a coordinate having a value equal to or less than value of said second reference coordinate, and in which said time gain is increased corresponding to a coordinate having a value equal to or greater than said third reference coordinate.

6. A time gain controlling apparatus for controlling time gain for echo reception, comprising
    a tablet pointer;
    coordinate translating means for defining one of two dimensional coordinate of a position on a surface of said tablet pointer by an external object touching said surface and being sensed electrically to define said position as a coordinate on a time axis, and defining electrically the other of said two dimensional coordinates as a coordinate on a gain axis; and
    controlling means for controlling time gain based on said two dimensional coordinates, said controlling means comprising:
        means for determining said time gain depending on value of said coordinate on said gain axis;
        means for increasing said time gain corresponding to a coordinate on one side with respect to a first reference coordinate on said gain axis; and
        means for decreasing said time gain corresponding to a coordinate on the other side with respect to said first reference coordinate.

7. The apparatus of claim 6, wherein said means for increasing comprises means for keeping constant change rate of said time gain.

8. The apparatus of claim 7, wherein said change rate corresponds to a difference between said coordinate and said reference coordinate on said gain axis.

9. The apparatus of claim 6, wherein said controlling means comprises:
    means for determining said time gain depending on value of a coordinate between a second reference coordinate on said gain axis and a third reference coordinate on said gain axis having a larger value than value of said second reference coordinate;
    means for decreasing said time gain corresponding to a coordinate having a value equal to or less than said second reference coordinate; and
    means for increasing said time gain corresponding to a coordinate having a value equal to or greater than said third reference coordinate.

10. The apparatus of claim 6, wherein said controlling means comprises means for performing control by selectively switching among:
    a mode in which said time gain is determined depending on value of a coordinate on said gain axis;
    a mode in which said time gain is increased corresponding to a coordinate on one side with respect to said first reference coordinate on said gain axis, and in which said time gain is decreased corresponding to a coordinate on the other side; and
    a mode in which said time gain is determined depending on value of a coordinate between a second reference coordinate on said gain axis and a third reference coordinate on said gain axis having a larger value than value of said second reference coordinate, in which said time gain is decreased corresponding to a coordinate having a value equal to or less than said second reference coordinate, and in which said time gain is increased corresponding to a coordinate having a value equal to or greater than said third reference coordinate.

11. A recording medium recorded in a computer readable manner with a program for causing a computer to implement the functions of:
    in controlling a time gain for echo reception, defining one of two dimensional coordinates of a position on a surface of a tablet pointer by an external object touching said surface and being sensed electrically to define said position as a coordinate on a time axis, and defining electrically the other of said two dimensional coordinates as a coordinate on a gain axis; and
    controlling the time gain based on said two dimensional coordinates, said controlling being performed by
        determining said time gain depending on value of the coordinate on said gain axis;
        increasing said time gain corresponding to a coordinate on one side with respect to a first reference coordinate on said gain axis; and
        decreasing said time gain corresponding to a coordinate on the other side with respect to said first reference coordinate.

12. The recording medium of claim 11, wherein rate of change of said increasing or decreasing of said time gain is constant.

13. The recording medium of claim 12, wherein said rate of change corresponds to a difference between said coordinate and said first reference coordinate on said gain axis.

14. The recording medium of claim 11, wherein said controlling is performed by:
    determining said time gain depending on value of a coordinate between a second reference coordinate on said gain axis and a third reference coordinate on said gain axis having a larger value than said second reference coordinate value;
    decreasing said time gain corresponding to a coordinate having a value equal to or less than said second reference coordinate; and increasing said time gain corresponding to a coordinate having a value equal to or greater than the value of said third reference coordinate.

15. The recording medium of claim 11, wherein said controlling is performed by:
selectively switching among:
a mode in which said time gain is determined depending on value of a coordinate on said gain axis;
a mode in which said time gain is increased corresponding to a coordinate on one side with respect to said first reference coordinate on said gain axis; and in which said time gain is decreased corresponding to a coordinate on the other side; and
a mode in which said time gain is determined depending on value of a coordinate between a second reference coordinate on said gain axis and a third reference coordinate on said gain axis having a larger value than value of said second reference coordinate, and in which said time gain is decreased corresponding to a coordinate having a value equal to or less than value of said second reference coordinate, and in which said time gain is increased corresponding to a coordinate having a value equal to or greater than value of said third reference coordinate.

16. An ultrasonic imaging apparatus comprising:
ultrasonic transmitting means for transmitting ultrasound;
echo receiving means for receiving echoes of said transmitted ultrasound;
time gain controlling, means for controlling a time gain for said reception;
image producing means for producing an image based on echo signals subjected to said time gain control; and
display means for displaying said produced image; wherein said time gain controlling means comprises:
a table pointer;
coordinate translating means for defining one of two dimensional coordinates of a position on a surface of said tablet pointer by an external object touching said surface and being sensed electrically to define said position as a coordinate on a time axis, and defining electrically the other of said two dimensional coordinates as a coordinate on a gain axis; and
controlling means for controlling the time gain based on said two dimensional coordinate, said controlling means comprising:
means for determining said time gain depending on value of the coordinate on said gain axis;
means for increasing said time gain corresponding to a coordinate on one side with respect to a first reference coordinate on said gain axis; and
means for decreasing said time gain corresponding to a coordinate on the other side with respect to said first reference coordinate.

17. The apparatus of claim 16, wherein means for increasing comprises means for keeping constant change rate of said time gain.

18. The apparatus of claim 17, wherein said change rate corresponds to a difference between said coordinate and said reference coordinate on said gain axis.

19. The apparatus of claim 16, wherein said controlling means comprises;
means for determining said time gain depending on value of a coordinate between a second reference coordinate on said gain axis and a third reference coordinate on said gain axis having a larger value than value of said second reference coordinate;
means for decreasing time gain corresponding to a coordinate having a value equal to or less than value of said second reference coordinate; and
means for increasing said time gain corresponding to a coordinate having a value equal to or greater than value of said third reference coordinate.

20. The apparatus of claim 16, wherein said controlling means comprises means for performing control by selectively switching among:
a mode in which said time gain is determined depending on value of a coordinate on said gain axis;
a mode in which said time gain is increased corresponding to a coordinate on one side with respect to said first reference coordinate on said gain axis, and in which said time gain is decreased corresponding to a coordinate on the other side; and
a mode in which said time gain is determined depending on value of a coordinate between a second reference coordinate on said gain axis and a third reference coordinate on said gain axis having a larger value than value of said second reference coordinate, and in which said time gain is decreased corresponding to a coordinate having a value equal to or less than value of said second reference coordinate, and in which said time gain is increased corresponding to a coordinate having a value equal to or greater than value of said third reference coordinate.

* * * * *